(12) United States Patent
Shaner et al.

(10) Patent No.: US 11,535,823 B2
(45) Date of Patent: Dec. 27, 2022

(54) HYBRID ALE YEAST STRAIN

(71) Applicant: Omega Yeast Labs, LLC, Chicago, IL (US)

(72) Inventors: Lance Shaner, Park Ridge, IL (US); Nate Gibbon, Chicago, IL (US)

(73) Assignee: OMEGA YEAST LABS, LLC, Chicago, IL (US)

( * ) Notice: Subject to any disclaimer, the term of this patent is extended or adjusted under 35 U.S.C. 154(b) by 184 days.

(21) Appl. No.: 16/710,884

(22) Filed: Dec. 11, 2019

(65) Prior Publication Data

US 2020/0255914 A1 Aug. 13, 2020

Related U.S. Application Data

(60) Provisional application No. 62/803,166, filed on Feb. 8, 2019.

(51) Int. Cl.
| | |
|---|---|
| C12C 11/09 | (2006.01) |
| C12N 1/18 | (2006.01) |
| A23L 2/38 | (2021.01) |
| A23L 33/14 | (2016.01) |
| C12C 12/00 | (2006.01) |
| C12R 1/865 | (2006.01) |

(52) U.S. Cl.
CPC .............. *C12N 1/185* (2021.05); *A23L 2/382* (2013.01); *A23L 33/14* (2016.08); *C12C 11/09* (2013.01); *C12C 12/006* (2013.01); *A23V 2002/00* (2013.01); *C12R 2001/865* (2021.05)

(58) Field of Classification Search
CPC ......... C12N 1/185; A23L 33/14; A23L 2/382; C12R 2001/865; A23V 2002/00; C12C 11/09; C12C 12/006
USPC .......................................................... 426/11
See application file for complete search history.

(56) References Cited

PUBLICATIONS

Stewart, G. G. et al. Pure and Appl. Chem. 59: 1493-1500 (Year: 1987).*
Tubb, R. S. et al. EBC Congress. 487-494 (Year: 1981).*

* cited by examiner

*Primary Examiner* — Hamid R Badr
(74) *Attorney, Agent, or Firm* — Marshall, Gerstein & Borun LLP

(57) ABSTRACT

The invention provides a hybrid ale strain of *Saccharomyces cerevisiae* and uses thereof.

1 Claim, No Drawings

HYBRID ALE YEAST STRAIN

PRIORITY

This patent application claims the benefit of priority to U.S. Provisional Patent Application Ser. No. 62/803,166, filed Feb. 8, 2019, which is incorporated by reference herein in its entirety.

FIELD OF THE INVENTION

The disclosure generally relates to a hybrid ale brewing strain of *Saccharomyces cerevisiae* and uses thereof.

BACKGROUND OF THE INVENTION

Ales are beers fermented at relatively warm temperatures (18° C. to 24° C.) by strains of *Saccharomyces cerevisiae*. Some ale strains possess genes (e.g., STA1, STA2, and STA3) encoding secreted glucoamylase enzymes that catalyze the release of glucose from starches and dextrins. Such strains are referred to as *S. cerevisiae* var. *diastaticus*. *S. cerevisiae* var. *diastaticus* strains are typically also Phenolic Off Flavor positive (POF+). POF+ refers to the ability of strain to catalyze the conversion of ferulic acid to 4-vinyl guaiacol, which has the flavor and aroma of cloves. This conversion is catalyzed by the gene product of FDC1. In some cases, such as in German-style Hefeweizen ales and Belgian Ales, this is an expected and desired flavor. In many beer styles, however, 4-vinyl guaiacol is considered an off-flavor.

There are not currently existing many options for ale yeasts that are both diastatic and POF–. Such strains would be useful in creating highly attenuated beers with clean flavors. Diastatic, POF– strains could also be useful for creating low calorie beers because most of the dextrins not typically consumed by yeast can be metabolized by diastatic strains, resulting in a product with less carbohydrates.

Most yeast strains available to brewers are derived from strains used by breweries around the world for centuries. Little effort has been made to hybridize existing brewing strains to create strains with novel combinations of characteristics. Blending strains can lead to unpredictable results and beers pitched with yeast blends cropped from previous batches often have different ratios of the strains originally pitched. Thus, there exists a need in the art for novel ale brewing strains that possess diastatic activity without producing 4-vinyl guaiacol.

SUMMARY OF THE INVENTION

The disclosure provides a hybrid ale brewing strain of *Saccharomyces cerevisiae* and uses thereof. In one aspect of the disclosure, there is provided an isolated yeast cell that is a lab-created hybrid of two publicly available ale strains, designated Parent A and Parent B. Parent A is marketed and sold by Omega Yeast Labs LLC under the strain number OYL-026 and is STA1+ and POF+. Parent B is marketed and sold by Omega Yeast Labs LLC under the strain number OYL-005 and is STA1– and POF–. The hybrid yeast strain (hereinafter referred to as "005/026 hybrid segregant"; deposited as accession no. NCYC 4330) of Parent A and Parent B was created by mating Parent A and Parent B using a selection scheme, followed by re-sporulating and germinating a resulting hybrid to segregate out the POF+ trait and maintain the STA1+ trait. The resultant yeast strain does not contain recombinant DNA.

In one aspect, the disclosure provides an isolated hybrid yeast cell 005/026 hybrid segregant of Parent A and Parent B deposited as accession no. NCYC 4330, or progeny thereof.

The present disclosure also provides a method for preparing a yeast cell culture by propagating a 005/026 hybrid segregant yeast cell as provided herein or from a culture as disclosed herein; and obtaining the 005/026 hybrid segregant yeast cell culture.

The present disclosure also provides a method of preparing a fermented product by contacting a source of sugar with a 005/026 hybrid segregant yeast cell from a strain as disclosed herein or from a culture as disclosed herein; conducting a fermentation process; and obtaining the fermented product. In some embodiments, the fermented product is a beverage. In some embodiments, the beverage is beer, sake, vodka, malt whiskey, wine, cider, brandy, mead, root-beer, ginger-beer, kefir or kumis. In some embodiments, the fermented product is a food. In some embodiments, the food is a yeast paste, a yeast extract, a probiotic, a food supplement or a bread.

The present disclosure also provides for a fermented product obtained by a method as disclosed herein. The present disclosure also provides for a fermented beverage obtained by a method as disclosed herein. The present disclosure also provides for a fermented food obtained by a method as disclosed herein. The present disclosure also provides for a fermented beverage comprising a 005/026 hybrid segregant yeast cell from a strain as disclosed herein or from a culture as disclosed herein. In some embodiments, the beverage is beer, sake, vodka, malt whiskey, wine, cider, brandy, mead, root-beer, ginger-beer, kefir or kumis. In some embodiments, the beverage is alcoholic. In some embodiments, the beverage is non-alcoholic. In some embodiments, the product is a food. In some embodiments, the food is a yeast paste, a yeast extract, a probiotic, a food supplement or a bread. In some embodiments, the product is a beverage. In some embodiments, the beverage is beer, sake, vodka, malt whiskey, wine, cider, brandy, mead, root-beer, ginger-beer, kefir or kumis.

The present disclosure also provides a beer produced by conducting a fermentation process with a 005/026 hybrid segregant yeast cell from a strain as disclosed herein or from a culture as disclosed herein. The present disclosure also provides a 005/026 hybrid segregant yeast cell obtained from a beer as disclosed herein. The present disclosure also provides a 005/026 hybrid segregant yeast cell culture comprising 005/026 hybrid segregant yeast cells obtained from a beer as disclosed herein.

The present disclosure also provides methods for preparing a 005/026 hybrid segregant yeast cell culture comprising propagating a 005/026 hybrid segregant yeast cell from a beer as disclosed herein; and obtaining the 005/026 hybrid segregant yeast cell culture.

The present disclosure also provides a method of manufacturing a fermented beverage by conducting a wort production process; and conducting a fermentation process with a 005/026 hybrid segregant yeast strain as disclosed herein. In some embodiments, the method may further comprise conducting a malting process. In some embodiments, the fermented beverage is a beer. In some embodiments, the methods may further comprise adding hops during the wort production process. In some embodiments, the methods may further comprise a conditioning process.

The present disclosure also provides a kit for preparing a fermented product comprising a 005/026 hybrid segregant yeast cell from a strain as disclosed herein or from a culture as disclosed herein. In some embodiments, the kit is a home brew kit. In some embodiments, the fermented product is a beverage. In some embodiments, the beverage a beer, sake, vodka, malt whiskey, wine, cider, brandy, mead, root-beer, ginger-beer, kefir or kumis. In some embodiments, the fermented product is a food. In some embodiments, the food is a yeast paste, a yeast extract, a probiotic, a food supplement or a bread.

Other features and advantages of the present disclosure will become apparent from the following detailed description. It should be understood, however, that the detailed description and the specific example, while indicating specific embodiments of the disclosure, are given by way of illustration only, because various changes and modifications within the spirit and scope of the disclosure will become apparent to those skilled in the art from this detailed description. The entire document is intended to be related as a unified disclosure, and it should be understood that all combinations of features described herein are contemplated, even if the combination of features are not found together in the same sentence, or paragraph, or section of this document. In addition to the foregoing, the invention includes, as an additional aspect, all embodiments of the invention narrower in scope in any way than the variations specifically mentioned above. For example, if aspects of the invention are described as "comprising" a feature, embodiments also are contemplated "consisting of" or "consisting essentially of" the feature.

DETAILED DESCRIPTION OF THE INVENTION

The disclosure provides a novel hybrid ale yeast strain and uses thereof. Disclosed herein is a lab-created hybrid of two publicly available ale strains, designated Parent A and Parent B. The hybrid yeast strain is designated "005/026 hybrid segregant" and is deposited as accession no. NCYC 4330. Parent A is marketed and sold by Omega Yeast Labs LLC under the strain number OYL-026. Fermentation with Parent A results in ales with a spicy, estery, and citrusy character. Parent B is marketed and sold by Omega Yeast Labs LLC under the strain number OYL-005. Fermentation with Parent B results in beers that are fruity and clean (non-phenolic, average apparent attenuation of 69-75%). The 005/026 hybrid segregant strain of Parent A and Parent B described herein was created by mating and using a selection scheme. The resultant 005/026 hybrid segregant strain does not contain recombinant DNA. Fermentation of an all-malt wort with the 005/026 hybrid segregant yeast strain disclosed herein results in a beer with high attenuation similar to Parent A and the fruity and clean character of Parent B. The 005/026 hybrid segregant was confirmed to be POF− by streaking on plates containing ferulic acid and sniffing the plates after growth. While clove aroma could be detected with Parent A, no clove aroma was detected with Parent B or with the 005/026 hybrid segregant. The 005/026 hybrid segregant was confirmed to be STA1+ by PCR analysis and by phenotypic analysis. The 005/026 hybrid segregant consistently achieved 86-89% apparent attenuation compared to the average of 69-75% apparent attenuation with Parent B and average of 88-95% apparent attenuation with Parent A.

The present disclosure provides a novel hybrid yeast strain designated 005/026 hybrid segregant and deposited as accession no. NCYC 4330. This yeast strain may be used in the manufacture of a fermented beverage (e.g., beer).

The present disclosure provides methods for manufacturing fermented beverages, including, for example, beer. These methods comprise a series of processes, including: a malting process, a wort production process and a fermentation process. A malting process is a process in which a grain may be germinated to produce malt. After germination, the malt is kilned and its root removed. Optionally, the malt is ground or milled. Alternatively, a malt is obtained, including purchased from any commercial source, and used directly in a wort production process. In a wort production process, brewing water is added to the malt (e.g., obtained from a malting process or obtained from a commercial source of malts), thereby producing a mash by permitting enzymes in the malt to convert starch to sugars. In the process of manufacturing fermented beverages (e.g., beers) adjuncts (e.g., rice, starch) may also be added with brewing water. Mash is lautered and then boiled after hops are added. Such boiling treatment is performed to inactivate enzymes in the wort, to make the wort clear by precipitating proteins, to extract and isomerize hop components and/or to sterilize the ingredients. Subsequently, the extract of the wort may be adjusted by the addition of water to the wort after boiling. After cooling of the wort obtained in the wort production process, the wort is fermented. In a fermentation process, 005/026 hybrid segregant yeast is added thereby converting sugars in the wort to alcohol. Optionally, a conditioning process may be conducted at the end of the fermentation process to allow the fermented beverage (e.g., beer) to mature.

Fermented beverages may include those with alcohol of about 2 to about 15.0 weight %. Preferably, they include those with alcohol of about 4 to about 8 weight %. Adjusting the extract concentration in the wort production process can make final products with the desired concentration of alcohol.

The present disclosure provides methods of fermentation using 005/026 hybrid segregant yeast cells as described herein. Fermentation refers to and includes any process for propagating yeast. The present disclosure provides products of fermentation (e.g., fermented products) including, for example, fermented beverages or fermented foods. Fermented beverages may include, for example, grain-based beverages, fruit-based beverages, honey-based beverages, vegetable-based beverages and dairy-based beverages. Exemplary grain-based beverages may include beer, sake, vodka and malt whiskey. Exemplary fruit-based beverages may include wine, cider and brandy. Exemplary honey-based beverages may include mead. Exemplary vegetable-based beverages may include root beer and ginger beer. Exemplary dairy-based beverages may include kefir and kumis. Fermented foods may include, for example, yeast paste (e.g., nutritional yeast paste), yeast extracts, probiotics, food supplements and breads. Food supplements including as described herein may be used to make beverages (e.g., nutritional beverages).

EXAMPLES

The following is a non-limiting example of an aspect of the disclosure described herein. The example is given solely for the purpose of illustration and is not to be construed as limiting the disclosure, as many variations thereof are possible.

Example 1

This Example describes a beer fermented with the 005/026 hybrid segregant strain described herein.

A recipe for 3 gallons of wort consisted of the following:
5 pounds of Vienna malt
2 pounds of Pilsner malt The malts were milled and mashed with 150 F water for one hour. 3.5 gallons of sweet wort was obtained and boiled for one hour with one hops addition of 1.25 oz of Styrian Celeia at 60 minutes, 0.5 oz of Styrian Celeia at 15 minutes, and 0.5 oz of Styrian Celeia at flameout to obtain a wort of specific gravity 1.052. The pitch rate was 7 million 005/026 hybrid segregant cells per mL. The fermentation was initiated at 65° F. The fermentation proceeded rapidly and achieved a final gravity of 1.007 within 5 days, resulting in an alcohol percentage of 5.9% ABV and 86% apparent attenuation. The resultant beer was bottled with an appropriate amount of dextrose to induce a secondary fermentation in the bottle for carbonation.

At two weeks post-bottling, a tasting of the resulting beer was conducted. The beer fermented with 005/026 hybrid segregant exhibited a fruity, non-phenolic profile. The fruitiness was described as citrusy and peachy.

Example 2

This Example describes a beer fermented with the 005/026 hybrid segregant strain described herein.

A recipe for 3 gallons of wort consisted of the following:
6 pounds of 2-row Brewer's malt
1.25 pounds of Munich malt
1.25 pounds of Wheat malt The malts were milled and mashed with 152 F water for one hour. 3.5 gallons of sweet wort was obtained and boiled for one hour with one hops addition of 0.5 oz of Simcoe at 30 minutes, 0.5 oz Simcoe, 0.5 oz Centennial, and 0.5 oz Amarillo at 5 minutes, a hopstand at 180 F for 15 minutes with 0.5 oz Simcoe, 0.5 oz Centennial, and 0.5 oz Amarillo to obtain a wort of specific gravity 1.074. The pitch rate was 14 million 005/026 hybrid segregant cells per mL. The fermentation was initiated at 68° F. A Dry Hop addition of 0.5 oz Centennial and 0.5 oz Amarillo was made on day 3. A second Dry Hop addition of 0.5 oz Centennial and 0.5 oz Amarillo was made on day 6.

The fermentation proceeded rapidly and achieved a final gravity of 1.009 within 7 days, resulting in an alcohol percentage of 8.5% ABV and 87% apparent attenuation. The resultant beer was bottled with an appropriate amount of dextrose to induce a secondary fermentation in the bottle for carbonation.

At two weeks post-bottling, a tasting of the resulting beer was conducted. The beer fermented with 005/026 hybrid segregant exhibited a hoppy, fruity, non-phenolic profile. The fruitiness was described as tropical, citrusy, and peachy.

Taken together, these studies validate the methods employed to create hybrid strains of existing ale yeasts with novel combinations of traits.

What is claimed:

1. A *S. cerevisiae* deposited as accession no. NCYC 4330, or progeny thereof.

* * * * *